July 4, 1972 R. KORDES Plant Pat. 3,229
ROSE PLANT
Filed Dec. 28, 1970
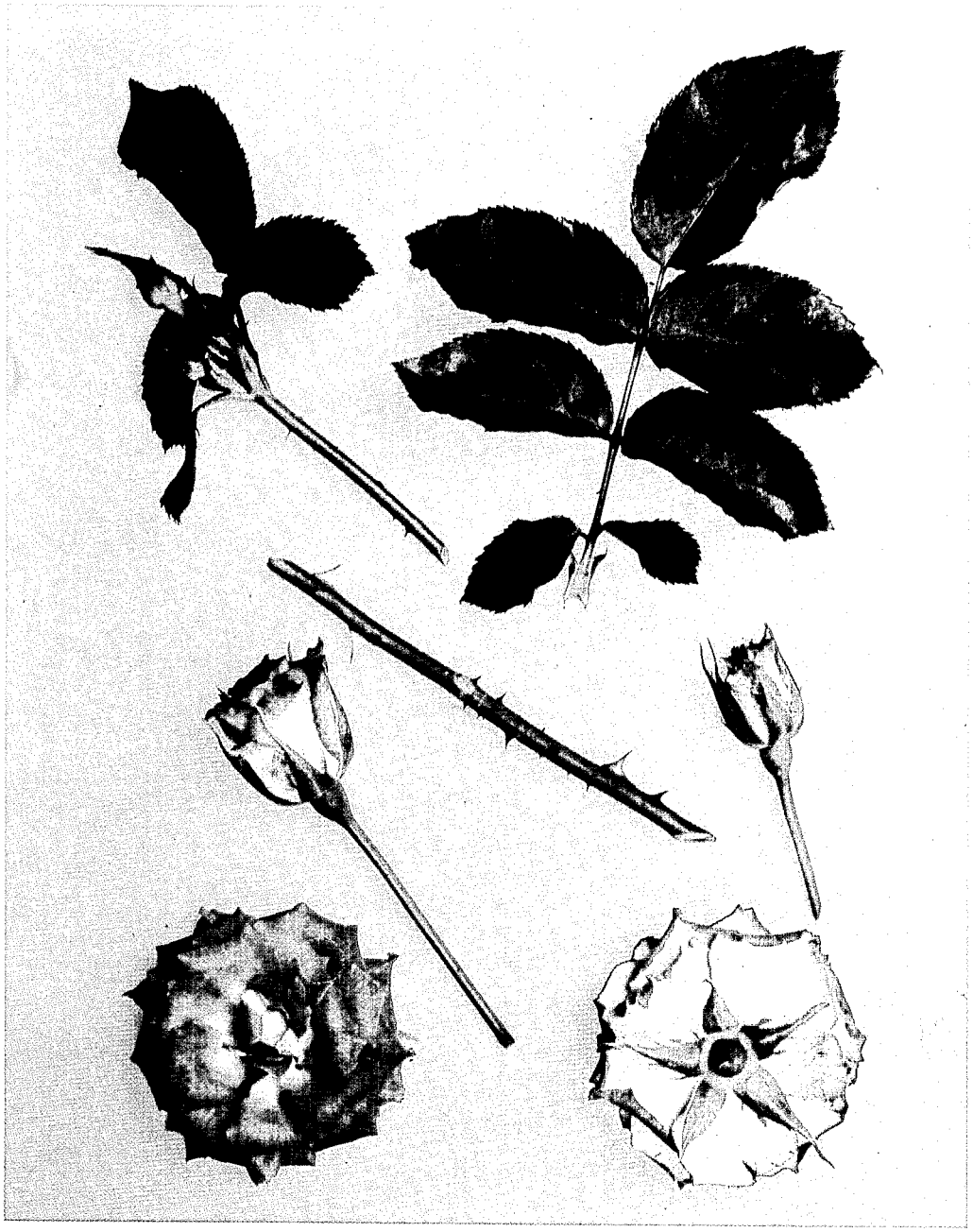
Inventor.
Reimer Kordes
By: Robb & Robb
Attorneys.

United States Patent Office

Plant Pat. 3,229

Patented July 4, 1972

3,229

ROSE PLANT

Reimer Kordes, Sparrieshoop, near Elmshorn, Holstein, Germany, assignor to Jackson & Perkins Company, Medford, Oreg.

Filed Dec. 28, 1970, Ser. No. 102,274

Int. Cl. A01h *5/00*

U.S. Cl. Plt.—22 1 Claim

The present invention relates to a new and distinct variety of rose plant of the floribunda class, which was originated by me by crossing the rose variety known as "Konigen der Rosen" (unpatented) with the rose variety known as "Zorina" (U.S. Plant Patent No. 2,321), the former being the seed parent and the latter being the pollen parent.

The primary objective of this breeding was to produce a new and improved rose variety of the floribunda class, which bears brightly bi-colored flowers suitable for both outdoor and greenhouse grown cut-flower use. This objective was fully achieved, along with other desirable improvements, as evidenced by the following unique combination of characteristics which are outstanding in the new variety and which distinguish it from its parents, as well as from all other rose varieties of which I am aware:

(1) A bushy and compact plant habit when grown outdoors;
(2) Exceptionally stiff and erect stems;
(3) An unusually vivid flower color in both the half-open and open flowers, corresponding to Capsicum Red on the upper surface of the petals and fading from Orange Buff to nearly white on the reverse of the petals; and
(4) Little or no flower fragrance.

Asexual reproduction of my new variety by budding, as performed by me in Germany and on my behalf at Wasco, Calif., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasinably possible to make the same in a color illustration of this character.

The following is a detailed description of the new rose variety, with color terminology in accordance with Wilson's Horticultural Colour Chart, except where general color terms of ordinary dictionary significance are obvious:

Parentage: Seedling.
*See parent.*—"Konigen der Rosen."
*Pollen parent.*—"Zorina."
Classification:
*Botanic.*—*Rosa hybrid.*
*Commercial.*—Floribunda.
Progagation: Hold its distinguishing characteristics through succeeding propagations by budding.

*Flower*

(Observations made from specimens grown in a greenhouse at Irvine, Calif., U.S.A., during the afternoon and late in the month of November.)

Blooming habit: Recurrent—continuous.
Bud:
*Size.*—About 1½ inches long when petals start to unfurl.
*Form.*—Long; blunt top.
*Color.*—When sepals first divide—Buttercup Yellow, Plate 5/1 on lower quarter of petals, gradually darkening to Cadmium Orange, Plate 8/1 which is heavily overlaid with Scarlet, Plate 19/1 especially near the petal edges. When half-blown—inside of petals—Lemon Yellow, Plate 4/1 on lower quarter, gradually overlaid with Capsicum Red, Plate 715 near petal edges, and with center area being Fire Red, Plate 15; reverse of petals—Lemon Yellow, Plate 4 at base of petals, blending gradually into Orange Buff, Plate 507, and overlaid near edges with Capsicum Red, Plate 715.

*Sepals.*—3 sepals lightly appendaged and 2 unappendaged sepals with hairy edges. Color—outside—Spinach Green, Plate 0960/1, streaked with Pod Green, Plate 061/2, and with base of sepals being Pod Green, Plate 061/2; inside—Lighter than Spinach Green, Plate 0960/3 and slightly tomentose.
*Receptacle.*—Color—Scheele's Green, Plate 860/3. Shape—funnel. Size—long. Surface—smooth.
*Peduncle.* — Length — medium. Surface — slightly prickly. Color—Scheele's Green, Plate 860/3. Strength—stiff; erect.
*Opening.*—Petals fold outwardly in a relatively flat conformation.

Bloom:
*Size.*—Large. Average size when fully expanded—3½ inches.
*Borne.*—Both singly and in flat clusters.
*Stems.*—Medium length.
*Form (when first open).*—Flat, with high center. Permanence—Retains its form to the end.
*Petalage.*—Number of petals under normal conditions—from 30 to 35.
*Color.*—Center of flower—upper side of petals—Lemon Yellow, Plate 4/1 on lower quarter of petals, changing to Capsicum Red, Plate 715/3, with center area darkening to Capsicum Red, Plate 715 near outer edge; reverse side of petals—Lemon Yellow, Plate 4 at base, blending gradually into Orange Buff, Plate 507, and overlaid near edges with Capsicum Red, Plate 715. Outer petals—same as center petals.
*General tonality from a distance.*—Capsicum Red, Plate 715.
*Discoloration.*—No change at end of first day, but by third day becoming Signal Red, Plate 719 on upper side of petals, with reverse side near white and overlaid especially at edges with Turkey Red, Plate 721.
*Fragrance.*—Very little.

Petals:
*Texture.*—Thin; quite rigid.
*Surface.*—Inside—satiny. Reverse—satiny.
*Shape.*—Round.
*Form.*—Flat; tips slightly recurved.
*Arrangement.*—Imbricated.
*Petaloids in center.*—Few.
*Persistence.*—Drop off cleanly.
*Lasting quality.*—On the plant—very long. As cut flower—very long.

*Reproductive organs*

Anthers: Small; few; arranged regularly around styles. Color—Yellow.
Filaments (threads)—Short. Color—Yellow.
Pollen: Color—Lemon yellow.
Styles: Loosely separated; uneven length; thin.
Stigmas: Color—Yellow.
Ovaries: Some protruding from calyx.
Fruit: None observed.

*Plant*

Form: Bush.
Growth: Vigorous; upright; compact.

Foliage: Compound of 5 or occasionally 7 leaflets on normal mid-stem leaves.

*Size.*—Large.

*Quantity.*—Normal.

*Color.*—New foliage—darker than Oxblood Red, Plate 00823. Old foliage—slightly darker than Spinach Green, Plate 0960.

*Leaflets.* — Shape — oval pointed. Texture—upper side—smooth. Ribs and veins—ordinary. Edge—serrated. Serration — single; small. Petiole (rachis) — Color — Green; under side—Small prickles. Stipules—short; serrated.

*Disease resistance.*—Resistant to mildew, as determined by comparison with other rose varieties grown under the same conditions at Irvine, Calif., U.S.A.

Wood:

*New wood.*—Color—Light green. Bark—smooth.

*Old wood.*—Color—Green. Bark—smooth.

Thorns:

*Thorns.*—*Quantity*—on main stalks from base—ordinary; on laterals from stalk—ordinary. Form— broad base; long; slightly hooked downward. Color (when young)—Red. Position—irregular.

*Prickles.*—Quantity—on main stalks—many; on laterals—many. Color—Red (same as thorns).

*Short needles.*—Quantity—on main stalks—none; on laterals—none.

I claim:

1. A new and distinct variety of rose plant of the floribunda class, substantially as herein shown and described, characterized particularly as to novelty by the unique combination of a bushy and compact plant habit when grown outdoors, exceptionally stiff and erect stems, an unusually vivid flower color in both the half-open and open flowers, corresponding to Capsicum Red on the upper surface of the petals and fading from Orange Buff to nearly white on the reverse of the petals, and little or no flower fragrance.

No references cited.

ROBERT E. BAGWILL, Primary Examiner